United States Patent [19]

Anderson et al.

[11] Patent Number: 4,947,578

[45] Date of Patent: Aug. 14, 1990

[54] CONTROLLED RELEASE SYSTEM FOR INSECT ATTRACTANT

[75] Inventors: Douglas G. Anderson, Lakeville; Keith D. Lokkesmoe, Burnsville, both of Minn.

[73] Assignee: Ecolab Inc., St. Paul, Minn.

[21] Appl. No.: 368,042

[22] Filed: Jun. 16, 1989

[51] Int. Cl.$^5$ .............................. A01M 1/20
[52] U.S. Cl. ........................................ 43/131
[58] Field of Search ............... 43/107, 114, 122, 131; 426/1; 424/84

[56] References Cited

U.S. PATENT DOCUMENTS

| | | | |
|---|---|---|---|
| 2,187,276 | 1/1940 | Miller | 43/131 |
| 2,254,948 | 9/1941 | Kubalek | 43/131 |
| 2,383,960 | 9/1945 | Dupuy | 43/131 |
| 3,032,915 | 5/1962 | Giroud-Abel | 43/131 |
| 3,575,346 | 4/1971 | Roth | 43/131 |
| 3,605,321 | 9/1971 | Lazarus | 43/131 |
| 3,770,199 | 11/1973 | Hoek et al. | 239/54 |
| 3,924,622 | 12/1975 | Brooke | 43/131 |
| 4,160,335 | 7/1979 | Von Kohorn et al. | 43/131 |
| 4,161,283 | 7/1979 | Hyman | 239/55 |
| 4,202,129 | 5/1980 | Greenberg | 43/131 |
| 4,445,641 | 5/1984 | Baker et al. | 239/6 |
| 4,548,764 | 10/1985 | Munteanu et al. | 261/75 |
| 4,562,794 | 1/1986 | Speckman | 119/156 |

OTHER PUBLICATIONS

Jaffe et al article entitled "Controlled-Released Reservoir Systems for the Delivery of Insect Seroid Analogues Against Ticks".
Weisner et al. article entitled "Development of an Effusion Regulated Controlled Release Device".

*Primary Examiner*—Kurt Rowan
*Attorney, Agent, or Firm*—Merchant, Gould, Smith, Edell, Welter & Schmidt

[57] ABSTRACT

A controlled release system for volatile liquid insect attractant compositions can be formed from a container having an aperture closed by a membrane, wherein the dimensions of the container, the dimensions of the aperture, the nature of the membrane, the liquid level, and vapor space within the container are conformed to produce an effective attractant release rate.

27 Claims, 2 Drawing Sheets

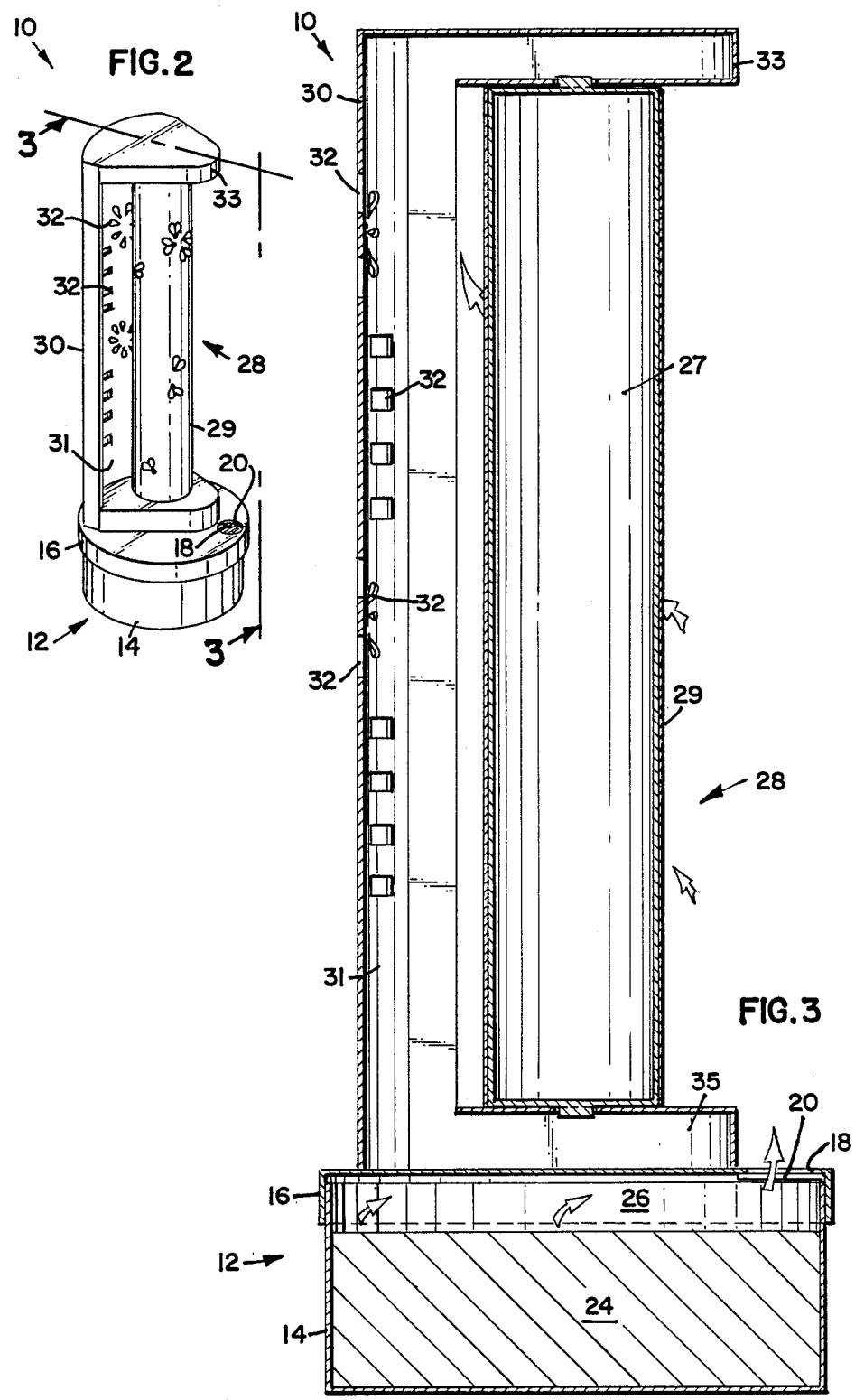

CONTROLLED RELEASE SYSTEM FOR INSECT ATTRACTANT

FIELD OF THE INVENTION

The invention relates to a system for the controlled release of a volatile liquid attractant for insect pests. More particularly, the invention relates to a release device for a volatile liquid ethanolic attractant for common flies, typically *Musca domestica*, wherein the liquid attractant is released as a vapor at a controlled rate for the purpose of attracting the insect pests. While the release rate of the attractant slowly declines, it remains at a highly effective level until the attractant is consumed.

BACKGROUND OF THE INVENTION

A great number of attractants for insect pests have been disclosed in the art. Such attractants comprise typically fermented materials or hydrolyzed proteinaceous materials which release volatile ingredients into the atmosphere, which tend to attract pests including flying insect pests. The released volatile materials include a vast array of volatile compositions including alcohols, aldehydes, amines, hydrocarbons, etc. Ethanol has been identified as one component of such natural attractant compositions. These compositions have been used without significant control over release rates. Many volatile compositions having some risk of flammability have been avoided as attractants because of safety considerations. To the best of our knowledge, no effective commercially successful control release system for neat, volatile attractants, such as ethanol, has been developed in the prior art.

Further, our review of the literature in this area indicates that volatile attractants, such as ethanol alone or in combination with other volatile components, have attracted no effective commercial attention, and the prior art provides no teaching with respect to the effective release rate for ethanolic attractants.

In large part, the use of controlled release systems for insect attractants has been directed to dispensing a variety of pheromones from a composition that can release the pheromone at their inherently low effective concentration. Pheromones are most commonly impregnated into porous plastic or onto natural materials such as corncob grits. Therefore, a great need exists for a controlled release device for a volatile attractant composition in which the device exhibits an effective release rate of attractant that continues to maintain a useful attracting concentration of the attractant in the environment during the useful life of the device. While the rate may slowly decline, the components of the controlled release device cooperate to maintain an effective release rate for the volatile attractant that can continue to attract pests, including flying insect pests, until the attractant is consumed.

SUMMARY OF THE INVENTION

The invention relates to a container having an aperture closed by a membrane wherein the geometry of the container, the semi-permeable membrane, and the size of the aperture cooperate to release an effective concentration of the volatile attractant vapor into the environment at a rate that maintains attractancy until the attractant is fully dispersed or consumed. We have found that the distance between the membrane and the surface of the volatile liquid held within the container affects the release rate of the vapor. We have designed the container to insure the vapor space remains saturated by attractant vapor and to minimize the change in height of the vapor space over time to dispense the attractant. The membrane materials and the orifice size, taken in conjunction with the container dimensions, permit vapor diffusion at a controlled rate such that the device continues to attract flying insects until the volatile liquid is entirely dispensed from the container. The preferred membrane materials additionally prevent liquid penetration through the membrane to enhance the safety of the controlled release system. The container can be configured to provide an effective amount of attractant vapor for up to 6 months.

In greater detail, we have further found that a volatile ethanolic attractant for flying insect pests, particularly flies of the order Diptera including *Musca domestica*, the common household fly, can be effectively controlled using the controlled release system of the invention to provide improved attractancy. For the purposes of this invention, semi-permeable means that attractant vapor can penetrate the membrane while attractant liquid is retained within the container.

BRIEF DESCRIPTION OF THE DRAWINGS

FIG. 2 is a perspective view of a flying insect trap incorporating the present controlled release system of the invention.

FIG. 3 is a cross-sectional view of the flying insect trap used with the controlled release system taken generally along the line 3—3 in FIG. 2.

DETAILED DISCUSSION OF THE INVENTION

Figure 1:
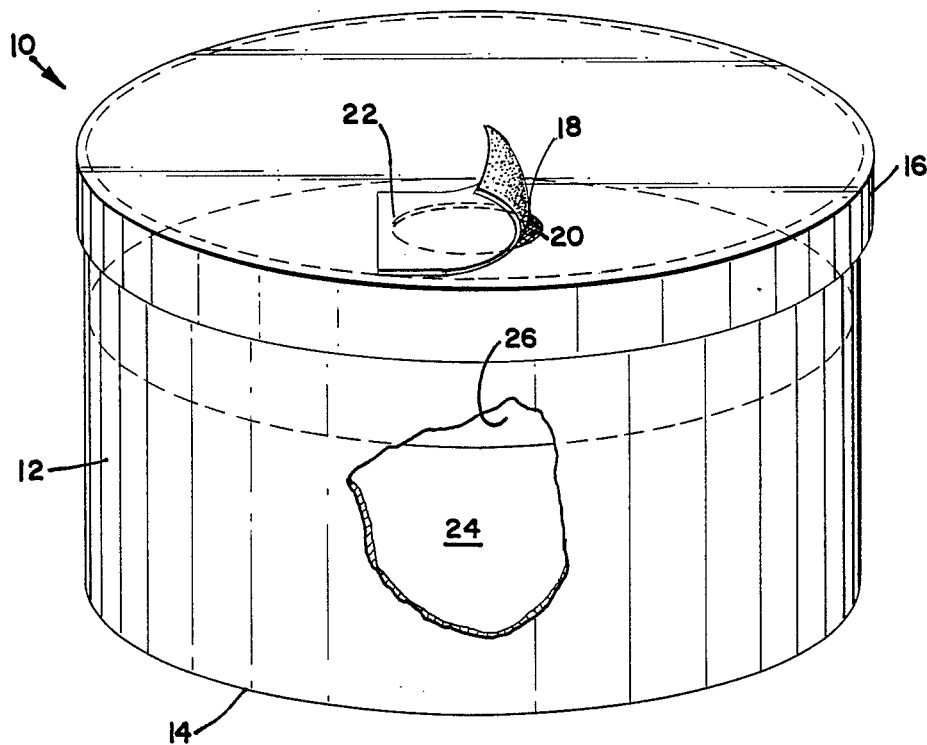
FIG. 1 is a perspective view of a preferred control release system of the invention.

Containers for the fly attractant useful in the invention can take any convenient shape. The containers can be spheroidal, cylindrical, in the form of a cube, a rectangular prism, an oval prism, pyramidal, etc. The preferred shape for the container of the invention is cylindrical, an oval-shaped prism, or a rectangular-shaped prism. The overall dimensions of the container are important in preventing a large change in the distance between the surface of the volatile liquid/vapor interface and the semi-permeable membrane. We have found that the rate of vapor transfer through the membrane decreases as the height of the vapor space increases. Accordingly, the diameter or length and width of the container is greater than the depth.

For a container holding 50 to 2000 gms of volatile liquid attractant, preferably holding 100 to 500 gms of fly attractant, the cylindrical container should have a radius of 3 to 15 cm, preferably 5 to 12 cm, and a depth of 2 to 15 cm, preferably 3 to 8 cm. A container having the form of a rectangular prism can have a length of about 5 to 10 cm, the width being less than the length, and a depth of from about 3 to 5 cm.

The container can be prepared from any barrier material capable of preventing any significant molecular diffusion or permeation of the attractant through the material. Typical barrier materials for the fly attractants of this invention include metals such as aluminum or steel sheet, thermoplastic materials such as polyethylene, polypropylene, polyester (polyethylene terephthalate, polybutylene terephthalate), etc. The choice of materials is not critical except that the barrier material should be inert to insect attractants, be moldable or shapeable into the container of the invention, and can be easily assembled.

The controlled release device for a volatile attractant of the invention is designed to have a service life of at least 1 week at a temperature of about 60° to 100° F. at a release rate of at least about 0.02 gm/hr. Preferably, the service life of the device is greater than 2 weeks, and can be as much as 6 months or more. More preferably, the service life of the device is from about 4 weeks to 8 weeks. Accordingly, at ambient temperatures, generally about 70°-85° F., the device should contain at least about 8.5 to 17 grams of the attractant to release about 0.05 to 0.1 grams of the attractant per hour to provide the minimum 1-week service life. For longer service life, for example, 2 weeks, the container should hold about 17 to 35 grams of the attractant to provide a service life at a release life of about 0.05 to 0.1 grams per hour. For a device having a service life of from 4 to 6 weeks, the container can hold about 35 to 100 grams of the attractant material to operate at a release rate of about 0.05 to 0.1 grams per hour for the service life. A controlled release system having a service life of 6 months can require about 250 to 500 gms of attractant to last for 6 months at a release rate of 0.05 to 0.1 gm/hr. If higher temperatures are expected, the rate of release will increase in proportion to the vapor pressure increase of the liquid attractant.

In order to provide additional guidance for design of the release system, a mathematical model was developed for describing ethanol evaporation through semipermeable membranes. This model will allow one to predict the evaporation rate as a function of time, temperature, and membrane/liquid area ratio. The rate is shown to vary with the inverse of the distance between the liquid/vapor interface and the porous membrane. The rate also varies with temperature in a manner proportional to the vapor pressure of ethanol at that temperature. Finally, the rate decreases as the ratio of membrane area to liquid surface area (Am/Ao) raised to some power n which is less than 1. The general equation of the model is as follows:

$$dw/dt = \frac{kS\,(Am/Ao)^n(2a)}{L^{(1/a-1)}}$$

dw/dt = evaporation rate (g/hr)
k = rate constant (cm²/hr)
S = grams of attractant liquid per unit height in cms of reservoir
L = vapor space distance (cm)
n = constant between 0.5 and 1.0
Am = membrane area (cm²)
Ao = liquid surface area (cm²)
a = constant between 0.5 and 0.9

The rate constant k varies with temperature by:

$$k = (k_o)\,10\,\text{EXP}\,1482\,\frac{1}{T_o - 56.43} - \frac{1}{T - 56.43}$$

where ko = rate constant in cm²/hr (usually between 0.01 and 0.10 cm²/hr) measured at some reference temperature To (temperature is in degrees Kelvin). EXP indicates a power of 10.

If the above differential equation is substituted with dw/dt = S dL/dt and solved by separation of variables, we obtain:

$$L = (L_o^{(1/a)} + 2(Am/Ao)^n kt)^a$$

where Lo = beginning vapor space distance at t = 0 and the rest of the variables are defined above. This model was tested against actual data and found to accurately predict the rate of evaporation once the parameters k, a, and n were determined for a particular container geometry.

The container has an aperture covered by a release membrane through which the attractant vapor is released into the environment. The aperture is conveniently of any shape. However, we have found that the circular or oval aperture is most easily manufactured. The aperture can be about 0.1 to 5 cm in diameter, preferably 0.2 to 2 cm. We have found that the size of the aperture and the vapor space distance between the liquid surface and the membrane are important in controlling the release rates. A desired ratio between the area of the aperture and the area of the liquid surface is about 0.01 to 0.1, preferably about 0.01 to 0.025, and, most preferably, about 0.01 to 0.02 to ensure the optimal release rate of the attractant from a liquid surface area ranging from about 50 to 80 cm². We have found that as the vapor space between the liquid surface and the aperture increases, the release rates are reduced. Accordingly, the distance between the liquid/vapor interface (liquid surface) and the semipermeable membrane should not change more than about 5 cm, preferably less than 4 cm, most preferably less than 3 cm during the useful service life. As the dimension from the membrane to the surface of the liquid attractant increases, the attractant vapor molecules must traverse an increased average distance, thus reducing the rate of release through the membrane. The design of the container is overall adjusted to minimize the change in distance from the liquid to the membrane and to maximize the surface area of the liquid. All these modifications ensure the consistent release of an effective concentration of the attractant into the atmosphere.

Polymeric materials useful in preparing the membrane covering the aperture in this invention may be selected from a wide range of substances. A variety of materials can provide a semi-permeable membrane that, due to its internal structure or to the formation of microporous structure in the membrane, can release the attractant at a significant rate. The preferred membrane is a semipermeable membrane having a pore size of about 0.001 to 0.05 microns in diameter. Such membranes are typically formed by modifying a film of the material using known techniques to provide the desired pore size and then laminating the material in a woven or nonwoven fabric to provide mechanical strength. The membranes can be manufactured from a variety of polymers, copolymers and terpolymers derived from the polymerization of one or more ethylenically unsaturated monomeric materials. Such polymer materials include polyethylene, polypropylene, polyvinyl chloride, polyurethanes, polysiloxane, thermoplastic elastomers, rubbers, polyesters, nylons, polyamides, polytetrafluoroethylene, polychlorotrifluroethylene, etc. The thickness of the polymer layer will generally range between about 25 to 100 microns.

The membrane is typically sealed to the container at the aperture such that the vapor can only exit the container through the membrane. The membrane can be attached to the aperture using adhesive means, heat sealed means, mechanical seals, etc.

There are a variety of known attractants that can be used in the device of the invention. The device of this invention is primarily designed for use with volatile attractant compositions having a vapor pressure (at ambient conditions) of at least 30 mm Hg, preferably about 40 to 70 mm Hg.

A variety of volatile liquid compositions can be found having a vapor pressure within this useful range. One volatile attractant we have found that is useful in the controlled release system of the invention comprises absolute ethanol or denatured absolute ethanol. Such material can be dispensed by the controlled release device of the invention at a rate of about 0.02 to about 0.2 grams per hour for the purpose of attracting typically flying insect pests. Once attracted, they can be trapped, large populations can be sprayed, the change in the density of the flying insect populations can be monitored, etc.

A preferred attractant for use in the device of the invention comprises a major portion of an ethanol attractant and an effective amount (preferably 0.05 to 5 v/v-%) of a volatile $C_{1-5}$ alcohol ester of a $C_{1-3}$ carboxylic acid (most preferably 0.1 to 1 v/v-% by amyl acetate). We have found that the combination of these materials is a significantly better attractant than either ethanol or the volatile ester alone, and throughout the useful release ranges tested for this attractant, the material remains an attractant to flying pests. The liquid material has a very pleasant mild odor. At concentrations in the air typically used in attracting flying pests, the material provides a barely detectable low level of a background mild, somewhat fruity odor. Preferably, this preferred attractant matreial is dispensed into the environment at a rate of about 0.05 to 0.2 grams per hour to draw flying insects to the insect trap.

The device of this invention can be conformed to lure household flying insect pests. The typical flying insect pest attracted by the device of this invention are flies belonging to the order Diptera, including flies of such families of Phoridae, Psychodidae, Fungivoridae, Chloropidae, Calliphoridae, Sacrophagidae, Anthomyiidae, Muscidae and Drosophilidae. The primary flying insect pest attractant of the preferred device of the invention are flies of the Muscidae family and, in particular, *Musca domestica,* the common household fly.

The device of the invention can be used in conjunction with any trap, which can kill or entrap a significant portion of the fly population, thus removing that proportion of the fly population from the human environment. Such traps can simply be a mechanical trap or a reservoir in which the flies cannot exit once they have entered. The trap can comprise a layer of highly tacky pressure sensitive adhesive whereon the flies are trapped by the tacky surface layer. The trap can comprise charged mesh screens causing the immediate electrocution of the flies upon entry. Any means for trapping, stunning or killing the flies in conjunction with the device can be used.

DESCRIPTION OF THE PREFERRED EMBODIMENT

Referring to the drawings, wherein like numbers represent like parts throughout the several views, there is generally disclosed in FIG. 1 the controlled release system 10 for a liquid insect attractant 24. The system 10 includes a reservoir 12 having a base 14 and a lid 16. The lid 16 is sized and configured to form a vapor-proof seal with the reservoir 12. In the preferred embodiment, the reservoir 12 is generally cylindrical in shape. While it should be understood that many configurations, sizes and shapes of the reservoir 12 can be envisioned within the scope of this invention, the dimensions of the reservoir 12, as illustrated in FIGS. 1 and 2 of the preferred embodiment, are 8.2 cm in diameter by 5 cm in height. The reservoir 12 is made of a nonporous impermeable material. In the preferred embodiment, polyethylene and polypropylene have been found to perform satisfactorily.

The lid 16 includes an aperture 18. The aperture 18 is generally circular in the preferred embodiment. The aperture 18 is closed by a membrane 20. The membrane 20 is sized and configured to fit within or over the aperture 18 to seal the liquid 24 within the system 10. The membrane 20 is of the type which allows vapor to escape the reservoir while retaining liquid. Therefore, a semipermeable membrane may be utilized as well as a stretched material where the stretching introduces pores for release of vapor. The pores are preferably small enough to prevent passage of liquid while permitting permeation of attractant vapor. A chemically treated material may also be utilized where the treatment introduces holes into the material for escape of vapor. A stretched or expanded polypropylene membrane (Celgard) can be used in the present invention.

A cover 22 can be utilized with the present invention to seal the reservoir 12 until a user desires the vapor to escape the reservoir 12 through aperture 18. In the preferred embodiment, a nonporous impermeable or barrier material is adhered to lid 16 and covers aperture 18. The cover 22 may be heat sealed or adhered to the reservoir. The cover 22 may also be sized and configured to be press fit within aperture 18. The user will remove the cover 22 to use the present invention. In another preferred embodiment, an empty container 12 can be filled at the use site. In such an embodiment, the cover 22 is optional, and serves only to protect the membrane during shipment and storage.

The bulk of the liquid flying insect attractant 24 is contained within reservoir 12 for attracting the insects. Above the liquid is a vapor space or head space 26. A preferred liquid attractant 24 is an ethanol/amyl acetate mixture discussed above.

In FIGS. 2 and 3, an insect holding or retaining means 28 is shown mounted on the lid 16 of the present invention. It should be understood that the retaining means 28 need not be mounted on lid 16 but must be associated with reservoir 12 and aperture 18 in a manner which attracts insects within range of any retaining means.

In the preferred embodiment, the retaining means 28 includes a generally tubular shaped member 27 and a layer of tacky adhesive 29 to retain the insects. It should be understood that any configuration of member 27 may be utilized which is within the scope of this invention.

Although an adhesive surface trap 29 is shown in FIGS. 2 and 3, a mechanical or electrical trap may also be used to retain the insects, whereby the insect enters the trap but is unable to crawl or fly out.

As illustrated in FIGS. 2 and 3, a shield 30 is utilized in the preferred embodiment to hide the insects which have been caught from view of the user. The shield 30 includes a wall 31 having first and second flanges 33, 35 proximate each end. The shield 30 can be formed as an integral unit and can be constructed of plastic in the preferred embodiment. The wall 31 is of a semi-circular shape. The shield 30 is connected to reservoir 12 by an adhesive in a manner which does not block or cover aperture 18. Tubular member 27 fits within the flanges 33, 35 of shield 27 in the preferred embodiment In operation, the user will remove cover 22, if present, from aperture 18. The removal of cover 22 allows a vapor from the attractant 24 in the vapor space 26 to escape through membrane 20 of aperture 18. When the attractant is released, flying insects are drawn to the device where the insects are retained by insect-retaining means 28, thus, eliminating pests.

The rate of release of the flying insect attractant 24 is at least about 0.02, preferably 0.03 to 0.2 grams of attractant per hour in the preferred embodiment. This effective rate of release is achieved by means of combining the preferred area of the aperture/membrane 18 which is about 0.7 to 1.0 cm$^2$; the area of the liquid/vapor interface about 50 to 80 cm$^2$; the initial distance between the membrane and the attractant liquid vapor interface about 1 to 2 cm; and the temperature of the attractant 24. With the proper combination of these factors, significant volumes of attractant 24 may be released at a controlled rate over a period of 1 to 2 months. The result is a device with a consistent attractant vapor output over a prolonged service period resulting in effective insect attractancy during the service period.

As discussed above, the particular configuration, shape and combination of materials for the system can be varied to suit the particular results desired. For example, the reservoir dimensions affect the release rate of attractant. It has been found that a relatively wide, flat reservoir is optimal because the vapor space distance between the membrane and the liquid surface does not change significantly over time. With an optimal attractant, the level of attractant decreases without substantially affecting the release rate of the vapor.

TABLE I

RELEASE RATES FOR VARIOUS ATTRACTANTS

| ELAPSED TIME t (hrs) | RELEASE RATE FOR ATTRACTANT #1* (g/hr) | RELEASE RATE FOR ATTRACTANT #2** (g/hr) | RELEASE RATE FOR ATTRACTANT #3*** (g/hr) | TEMP °F. |
|---|---|---|---|---|
| 0.00 | | | | 82.4 |
| 17.65 | 0.116 | 0.123 | 0.097 | 83.8 |
| 48.38 | 0.116 | 0.120 | 0.103 | 86.0 |
| 65.67 | 0.119 | 0.128 | 0.116 | 84.2 |
| 89.80 | 0.124 | 0.126 | 0.109 | 86.0 |
| 161.60 | 0.122 | 0.127 | 0.110 | 87.8 |
| 185.33 | 0.123 | 0.126 | 0.113 | 87.8 |
| 209.17 | 0.127 | 0.129 | 0.117 | 87.8 |
| 233.78 | 0.111 | 0.108 | 0.097 | 78.8 |
| 257.92 | 0.115 | 0.116 | 0.102 | 84.2 |
| 330.18 | 0.113 | 0.115 | 0.102 | 88.7 |
| 354.00 | 0.104 | 0.104 | 0.095 | 85.1 |
| 377.68 | 0.103 | 0.102 | 0.093 | 82.4 |
| 401.40 | 0.108 | 0.105 | 0.094 | 85.1 |
| 425.25 | 0.107 | 0.104 | 0.094 | 84.2 |
| 497.32 | 0.109 | 0.107 | 0.096 | 86.0 |
| 529.77 | 0.107 | 0.106 | 0.098 | 84.2 |
| 553.55 | 0.109 | 0.105 | 0.097 | 84.2 |
| 570.25 | 0.113 | 0.106 | 0.099 | 86.0 |
| 593.93 | 0.114 | 0.107 | 0.096 | 86.0 |
| 665.70 | 0.107 | 0.102 | 0.097 | 85.1 |
| 689.78 | 0.110 | 0.104 | 0.093 | 86.9 |
| 742.92 | 0.103 | 0.100 | 0.092 | 87.8 |
| 833.50 | 0.097 | 0.090 | 0.082 | 87.8 |
| 857.53 | 0.099 | 0.089 | 0.087 | 85.1 |
| 880.45 | 0.107 | 0.096 | 0.092 | 86.0 |
| 905.83 | 0.101 | 0.098 | 0.092 | 86.0 |
| 932.00 | 0.101 | 0.094 | 0.088 | 86.0 |

*Attractant #1 is: Absolute Ethanol with 5% water added.
**Attractant #2 is: Absolute Reagent Ethanol (contains about 5% isopropyl alcohol and about 5% methanol).
***Attractant #3 is: Absolute Reagent Ethanol with 5% water (contains about 5% isopropyl alcohol, 5% methanol and about 5% water).

The data shown in Table I establishes that the controlled release means shown in FIG. 1 is effective to release a variety of attractants at a significant rate over an extended period. Over a 39-day period, the release rates varied somewhat, but showed a minimal continuing decline in rates of release. During the testing, the release rates remained well above the 0.02 gms/hr threshold required for attractants. The data shows that rates tend to increase with temperature. Overall, the controlled release system proved to be effective in release of a variety of attractants for an extended period.

While particular embodiments of the invention have been described, modifications of the invention will be apparent to those skilled in the art in light of the foregoing description. This description is intended to provide specific examples of certain embodiments which clearly and fully disclose the present invention. Accordingly, the invention is not limited to the described embodiments or to the use of the specific elements therein. All alternative modifications and variations of the present invention which follows in the spirit and broad scope of the appended claims are covered.

What is claimed is:

1. A controlled release device for a volatile liquid insect attractant composition, which device comprises:
   (a) an enclosure for the volatile attractant composition, said enclosure having an aperture;
   (b) a volatile insect attractant comprising ethanol, a volatile ester or a mixture thereof held within said enclosure; and (c) a membrane permeable to the attractant vapor covering said aperture;
wherein the device releases the attractant vapor at a rate of at least about 0.02 gm/hr.

2. The device of claim 1 wherein the membrane is impermeable to the liquid attractant.

3. The device of claim 1 wherein the enclosure is cylindrical.

4. The device of claim 1 wherein the aperture is circular.

5. The device of claim 1 wherein the vapor pressure of the attractant is at least 30 mm Hg at 75° F.

6. The device of claim 1 wherein the ester is a lower alkanol ester of acetic acid.

7. The device of claim 1 wherein the device releases attractant at a rate that maintains effective insect attractancy until the liquid attractant is consumed.

8. The device of claim 1 wherein the device is configured for flying insect pests.

9. The device of claim 8 wherein the device is conformed for *Musca domestica*.

10. A controlled release device for a volatile flying insect attractant composition, which device comprises:
    (a) an enclosure for the volatile attractant composition, said enclosure having an aperture;
    (b) a volatile insect attractant comprising ethanol, a volatile ester or a mixture thereof held within said enclosure; and
    (c) a membrane permeable to the attractant vapor covering said aperture;
wherein the device releases the attractant vapor at a rate of about 0.02 to 0.2 gm/hr, and wherein the device is conformed for an insect from the family Muscidae, Sarcophagidae, Calliphoridae, Drosophilidae, Phoridae, Psychodidae, or Fungivoridae.

11. The device of claim 10 wherein the enclosure is cylindrical.
    (b) a volatile insect attractant comprising ethanol, a volatile ester or a mixture thereof held within said enclosure; and
    (c) a membrane permeable to the attractant vapor covering said aperture;
wherein the device releases the attractant vapor at a rate of at least about 0.02 gm/hr.

12. The device of claim 10 wherein the membrane is impermeable to the liquid attractant.

13. The device of claim 10 wherein the aperture is circular.

14. The device of claim 10 wherein the vapor pressure of the attractant is at least 30 mm Hg at 25° F.

15. The device of claim 10 wherein the ester is a lower alkanol ester of acetic acid.

16. The device of claim 10 wherein the device releases attractant at a rate that maintains effective insect attractancy until the liquid attractant is consumed.

17. The device of claim 10 wherein the device is conformed for *Musca domestica*.

18. A controlled release system, for a volatile liquid attractant for *Musca domestica*, which device is conformed to produce an effective release rate of an attractant that can maintain attractancy until consumed, which device comprises:
    (a) a cylindrical enclosure, having a radius of about 5 to 15 cm and a depth of about 2 to 8 cm, for the volatile attractant composition, the enclosure having an aperture;
    (b) a volatile attractant comprising ethanol, held within said enclosure;
    (c) a semi-permeable membrane having a pore dimension of about 0.001 to 0.05 microns covering said aperture;
wherein the device can release the ethanolic attractant at a rate of about 0.02 to 0.2 gm/hr.

19. The device of claim 18 wherein the aperture is circular and the ratio of the aperture diameter to enclosure diameter is 0.01 to 0.1.

20. The device of claim 19 wherein the initial distance between the volatile liquid attractant and the aperture is at least 0.1 cm.

21. The device of claim 20 wherein the distance between the aperture and the liquid level is not more than 5 cm.

22. The device of claim 18 wherein the athanolic attractant comprises a major proportion of ethanol and about 0.05 to 5 v/v % of a volatile $C_{1-5}$ alkanol ester of acetic acid.

23. The device of claim 22 wherein the ethanolic attractant comprises a major proportion of ethanol and about 0.1 to 1 v/v % of amyl acetate.

24. The device of claim 18 wherein the semi-permeable membrane is a stretched polyolefin.

25. The device of claim 18 wherein the aperture is proximate to a means to entrap insect pests attracted by the device.

26. The device of claim 25 wherein the means to entrap comprises a surface having a coating of a pressure-sensitive adhesive.

27. The device of claim 18 wherein the cylindrical enclosure has a capacity of about 15 to 450 grams and wherein the aperture is in a surface exposed to the attractant vapor.

* * * * *

UNITED STATES PATENT AND TRADEMARK OFFICE
CERTIFICATE OF CORRECTION

PATENT NO. : 4,947,578

DATED : August 14, 1990

INVENTOR(S) : Douglas G. Anderson and Keith D. Lokkesmoe

It is certified that error appears in the above-identified patent and that said Letters Patent is hereby corrected as shown below:

At column 4, line 25, please delete "semipermeable" and substitute therefore --semi-permeable--.
At column 4, line 45, please delete "semipermeable" and substitute therefore --semi-permeable--.
At column 5, line 30, please delete "matreial" and substitute therefore --material--.
At column 6, line 15, please delete "semipermeable" and substitute therefore --semi-permeable--.
At column 10, line 33, please delete "athanolic" and substitute therefore --ethanolic--.

Signed and Sealed this

Twenty-second Day of December, 1992

Attest:

DOUGLAS B. COMER

Attesting Officer

Acting Commissioner of Patents and Trademarks